US008361480B2

(12) United States Patent
Harrus et al.

(10) Patent No.: US 8,361,480 B2
(45) Date of Patent: Jan. 29, 2013

(54) ATTENUATED EHRLICHIOSIS VACCINE

(75) Inventors: Shimon Harrus, Moshav Tal Shahar (IL); Gad Baneth, Kibbutz Tzora (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 122 days.

(21) Appl. No.: 12/677,343

(22) PCT Filed: Sep. 11, 2008

(86) PCT No.: PCT/IL2008/001216
§ 371 (c)(1),
(2), (4) Date: Jun. 7, 2010

(87) PCT Pub. No.: WO2009/034575
PCT Pub. Date: Mar. 19, 2009

(65) Prior Publication Data
US 2010/0239613 A1 Sep. 23, 2010

Related U.S. Application Data

(60) Provisional application No. 60/971,271, filed on Sep. 11, 2007.

(51) Int. Cl.
*A61K 39/02* (2006.01)
*C12N 1/20* (2006.01)
(52) U.S. Cl. .................. 424/234.1; 435/252.1
(58) Field of Classification Search .......... None
See application file for complete search history.

(56) References Cited

U.S. PATENT DOCUMENTS

| | | | |
|---|---|---|---|
| 4,235,877 A | 11/1980 | Fullerton | |
| 5,047,540 A | 9/1991 | Kamata | |
| 5,192,679 A | 3/1993 | Dawson | |
| 6,043,085 A | 3/2000 | Yu | |
| 6,306,394 B1 | 10/2001 | Murphy | |
| 6,392,023 B1 | 5/2002 | Walker | |
| 6,432,649 B1 | 8/2002 | Stich | |
| 6,458,942 B1 | 10/2002 | Walker | |
| 7,635,481 B2 * | 12/2009 | Hu et al. | 424/190.1 |
| 7,951,386 B2 * | 5/2011 | Chang | 424/278.1 |
| 2004/0121433 A1 | 6/2004 | McBride | |
| 2004/0126871 A1 | 7/2004 | Barbet | |
| 2004/0170972 A1 | 9/2004 | Chang | |
| 2005/0202046 A1 | 9/2005 | Hu | |
| 2006/0188524 A1 | 8/2006 | Hu | |
| 2006/0234322 A1 | 10/2006 | Krah | |

FOREIGN PATENT DOCUMENTS

WO 2003/038061 A1 5/2003

OTHER PUBLICATIONS

Harrus et al 1999 (J Clin Microbiol. September; 37(9): 2745-2749).*
Bowie, Michael V. et al., "Potential value of major antigenic protein 2 for serological diagnosis of heartwater and related Ehrlichial infections", Clin. Diagnostic Lab. Immun., 6(2):209-215 (1999).
Branger, S. et al., "Evaluation of antibiotic susceptibilities of *Ehrlichia canis*, *Ehrlichia chaffeensis*, and *Anaplasma phagocytophilum* by real-time PCR", Antimicrob. Agents Chemother., 48(12):4822-4828 (2004).
Breitschwerdt, Edward B. et al. "Doxycycline hyclate treatment for experimental canine Ehrlichiosis followed by challenge inoculation with two *Ehrlichia canis* strains", Antimicrobial Agents and Chemotherapy, 42(2):362-68 (1998).
Bremer, William G. et al., "Transstadial and intrastadial experimental transmission of *Ehrlichia canis* by male *Rhipicephalus sanguineu*", Vet. Parasitol., 131:95-105 (2005).
Chen, S.-M. et al., "Identification of the antigenic constituents of *Ehrlichia chaffeensis*", Am J Trop Med Hyg, 50 (1):52-58 (1994).
Chen, Sheng-Ming et al., "Western immunoblotting analysis of the antibody responses of patients with human monocytotropic ehrlichiosis to different strains of *Ehrlichia chaffeensis* and *Ehrlichia canis*", Clin Diag Lab Immunol, 4(6):731-735 (1997).
Dawson, Jacqueline E. et al., "Serologic diagnosis of human ehrlichiosis using two *Ehrlichia canis* isolates", J. Infect. Dis., 163(3):564-567 (1991).
Dawson, Jacqueline E. et al., "Human endothelial cells as an alternative to DH82 cells for isolation of *Ehrlichia chaffeensis*, *E. canis*, and *Rickettsia rickettsii*", Pathobiology, 61(5-6):293-296 (1993).
Faburay, Bonto et al., "Immunisation of sheep against heartwater in the Gambia using inactivating and attenuated *Ehrlichia ruminantium* vaccines", Vaccine 25(46):7939-7947 (2007).
Hadani, A. et al., "Some methods for the breeding of ticks in the laboratory", Isr. J. Vet. Med., 26:87-100 (1969).
Harrus, Shimon et al., "Canine monocytic ehrlichiosis—an update", Comp. Cont. Educ. Pract. Vet., 19(4):431-444 (1997).
Harrus, Shimon et al., "Amplification of Ehrlichial DNA from dogs 34 month after infection with *Ehrlicihia canis*", J. Clin. Microbiol., 36(1):73-76 (1998).
Harrus, Shimon et al., "Comparison of Simultaneous Splenic Sample PCR for Diagnosis and treatment of Experimental *Ehrlichia canis* infection", Antimicrob. Agents Chemother., 48:4488-4490 (2004).
Hemlet, Irene E. et al., "Serial propagation of *Ehrlichia canis* in primary canine peripheral blood monocyte cultures", Cornell Vet, 70:37-42 (1980).
Jongejan, Frans, "Protective immunity to heartwater (*Cowdria ruminatum* infection) is acquired after vaccination with in vitro-attenuated rickettsiae", Infection and Immunity, American Society for Microbiology, 59(2):729-731 (1991).
Keysary, Avi et al., "The first isolation in vitro propagation and genetic charachterization of *Ehrlichia canis* in Israel", Veterinary Parasitology, 62(3-4):331-340 (1996).
Keysary, Avi et al., "Cultivation of *Ehrlichia canis* in a continuous BALB/C mouse macrophage cell culture line", J. Vet. Diagn. Invest., 13(6):521-523 (2001).
Knowles, Tamece T. et al., "Characterization of the Major Antigenic Protein 2 of *Ehrlichia canis* and *Ehrlichia chaffeensis* and Its Application for Serodiagnosisof Ehrlichiosis", Clin. Diagn. Lab. Immunol., 10(4):520-524 (2003).

(Continued)

*Primary Examiner* — Padma Baskar
(74) *Attorney, Agent, or Firm* — Rodney J. Fuller; Booth Udall Fuller, PLC

(57) ABSTRACT

The present invention relates to an attenuated strain of *Ehrlichia canis* and a vaccine comprising said attenuated strain for protection of mammals against ehrlichiosis. The invention further relates to methods of preventing ehrlichiosis and of attenuating the pathogenicity *Ehrlichia canis*.

15 Claims, 2 Drawing Sheets

OTHER PUBLICATIONS

Lewis, George E. Jr. et al., "The brown dog tick *Rhipicephalus sanguineus* and the dog as experimental hosts of *Ehrlichia canis*", Am. J. Vet. Res., 38:1953-1955 (1977).

Mahan, Sunita et al., "A preliminary study to evaluate the immune responses induced by immunization of dogs with inactivated *Ehrlichia canis* organisms", Onderstepoort Journal of Veterinary Research, 72(2):119-128 (2005).

Mathew, J. S. et al., "Attempted transmission of *Ehrlichia canis* by *Rhipicephalus sanguineus* after passage in cell culture", Am. J. Vet. Res., 57(11):1594-1598 (1996).

McBride, Jere W. et al., "Glycosylation of homologous immunodominant proteins of *Ehrlichia chaffeensis* and *Ehrlichia canis*", Infection and Immunity, 68(1):13-18 (2000).

McBride, Jere W. et al., "Immunodiagnosis of *Ehrlichia canis* infection with recombinant proteins", J. Clin. Microbiol., 39(1):315-322 (2001).

Nyindo, M. B. A. et al., "Tropical canine pancytopenia: in vitro cultivation of the causative agent—*Ehrlichia canis*", Am. J. Vet. Res., 32(11):1651-1658 (1971).

Ohashi, Norio et al., "Cloning and charachterization of multigenes encoding the immunodominant 30-kilodalton major outer membrane proteins of *Ehrlichia canis* and application of the recombinant protein for serodiagnosis", J. Clin. Microbiol., 36(9):2671-2680 (1998).

Perez, Miriam et al., "Human infection with *Ehrlichia canis* accompanied by clinical signs in Venezuela", Ann NY Acad Sci., 1078:110-117 (2006).

Rikihisa, Yasuko, "Cross-reacting antigens between *Neorickettsia helminthoeca* and *Ehrlichia* species, shown by immunofluorescence and Western immunoblotting", J Clin Microbiol, 29(9):2024-2029 (1991).

Rikihisa, Yasuko et al., "Western immunoblot analysis of *Ehrlichia chaffeensis*, *E. canis*, or *E. ewingii* infections in dogs and humans", J Clin Microbiol, 32(9):2107-2112 (1994).

Ristic, Miodrag et al., "Serological diagnosis of tropical canine pancytopenia by indirect immunofluorescence", Infect. Immun., 6(3):226-231 (1972).

Samish, M. et al., "Transmission of *Theileria annulata* (Dschunkowsky & Luhs 1904) by *Hyalomma excavatum* (Koch 1844)", Parasitology, 86:269-274 (1983).

Stephenson, E. H. et al., "Canine peritoneal macrophages: cultivation and infection with *Ehrlichia canis*", Am J Vet Res., 38(11):1815-1819 (1977).

Stich, Roger W. et al., "Detection of *Ehrlichia canis* in canine carrier blood and in individual experimentally infected ticks with a p30-based PCR assay", J Clin Microbiol, 40(2):540-546 (2002).

Unver, Ahmet et al., "Molecular and antigenic comparison of *Ehrlichia canis* isolates from dogs, ticks, and a human in Venezuela", J Clin Microbiol., 39(8):2788-2793 (2001).

Unver, Ahmet et al., "Analysis of 16S rRNA gene sequences of *Ehrlichia canis*, *Anaplasma platys*, and *Wolbachia* species from canine blood in Japan", Ann NY Acad. Sci., 990:692-698 (2003).

Waner, Trevor et al., "Detection of platelet-bound antibodies in beagle dogs after artificial infection with *Ehrlichia canis*", Vet. Immunol. Immunopathol., 77(1-2):145-150 (2000).

Wellman, Maxey L. et al., "A macrophage-monocyte cells line from a dog with malignant histiocytosis", In Vitro Cell Develop Biol, 24:223-228 (1998).

Yu, Xue-Jie et al., "Molecular cloning and characterization of the 120-kilodalton protein gene of *Ehrlichia canis* and application of the recombinant 120-kilodalton protein for serodiagnosis of canine ehrlichiosis", J Clin Microbiol, 3(1):369-374 (2000).

Zweygarth, Erich et al., "An attenuated *Ehrlichia ruminantium* (Welgevonden stock) vaccine protects small ruminants against virulent heartwater challenge", Vaccine, 23:1695-1702 (2005).

* cited by examiner

ATTENUATED EHRLICHIOSIS VACCINE

RELATED APPLICATIONS

This application is the U.S. National Stage of PCT/IL2008/001216 filed Sep. 11, 2008, which claims the benefit of U.S. Provisional Application No. 60/971,271 filed Sep. 11, 2007 the contents of each of which are herein incorporated by reference for all purposes.

FIELD OF THE INVENTION

The present invention relates to an attenuated strain of *Ehrlichia canis* and a vaccine comprising said attenuated strain for protection of mammals against ehrlichiosis. The invention further relates to methods of preventing ehrlichiosis and of attenuating the pathogenicity *Ehrlichia canis*.

BACKGROUND OF THE INVENTION

Canine monocytic ehrlichiosis (CME) is a tick-borne rickettsial disease, affecting dogs and other canine species worldwide. The causative agent is *Ehrlichia canis*, which infects circulating lymphocytes and is transmitted transtadially by the brown dog tick *Rhipicephalus sanguineus*. CME occurs in acute and subclinical phases, and in some cases progresses to a chronic phase. The acute phase is characterized by fever, anorexia, depression, lymphadenopathy and mild thrombocytopenia. Dogs typically recover from the acute illness, but become persistently infected carriers of the organism without clinical signs of disease for months or even years. When it develops, the chronic phase is characterized by clinical signs including thrombocytopenia, hyperglobulinemia, anorexia, emaciation, and hemorrhage, particularly epistaxis, petechiae and ecchymoses, and may result in death. Pancytopenia characterizes the chronic phase of the disease and may persist for a period of months, or for the remaining life of the dog. Supportive therapy is often necessary to combat wasting and specific organ dysfunction.

Human monocytic ehrlichiosis (HME) is caused by the related organism *E. chaffeensis*, and is characterized by fever, headache, myalgia and leukopenia. Furthermore, a similar disease termed Venezuela Human Ehrlichiosis (VHE) has been determined to be caused by a strain of *E. canis* designated VHE AF373612 (Perez et al. (2006) Ann N Y Acad Sci. 1078:110-7). Antibiotic therapy, particularly with doxycycline or tetracycline, is used for treatment of CME, HME and VHE, and is mainly effective if initiated at an early disease stage. There is no commercial vaccine for any of the aforementioned diseases, and tick control remains the recommended prophylactic method.

A number of proposed vaccines against *E. canis* and methods of protection against *E. canis* infection are known in the prior art.

US Patent application publication Nos. 2005/0202046 and 2006/0188524 disclose a vaccine composition which comprises an inactivated *E. canis* bacterin, a carrier, and an adjuvant system; and a method for the prevention or amelioration of canine ehrlichiosis in a dog by administration of such a vaccine. The disclosed adjuvant system contains both an antibody response inducing agent e.g. EMA/NEOCRYL® (Ethylene Maleic Anhydride (EMA)/Neocryl), and a cell-mediated immunity response inducing agent e.g. Bacilli Calmette-Guerin (BCG) or EMULSIGEN (Oil-in-Water Emulsified Adjuvant). While these publications allege that the invention effectively induces immunity, the disclosed vaccines are in fact deficient, since a significant proportion of dogs immunized with the vaccines are reported to develop canine ehrlichiosis. In addition, preparation of such vaccines is costly, due to the inclusion of multiple adjuvants, and the requirement for inactivating the *E. canis* strains. Inactivation, according to these disclosures, is carried out by conventional means, including use of chemical inactivating agents such as binary ethyleneimine, beta-propiolactone, formalin, merthiolate, gluteraldehyde, sodium dodecyl sulfate, or mixtures thereof; heat, or psoralen in the presence of ultraviolet light.

Other prior art disclosures relate to vaccines comprising isolated *E. canis* antigens or combinations thereof, for example as disclosed in US Patent Application Publication No. 2006/0234322. U.S. Pat. Nos. 6,458,942 and 6,392,023 disclose recombinant forms of homologous 28-kDa immunoreactive proteins of *E. canis*, and a method of inhibiting *E. canis* infection by administration of a composition comprising such antigens. US Patent Application Publication No. 2004/0170972 discloses the *E. canis* recombinant proteins ProA, ProB, mmpA, and a cytochrome oxidase homolog, and use thereof for a recombinant vaccine. US Patent Application Publication No. 2004/0126871 discloses a DNA vaccine comprising the gene for major antigenic protein-1 (MAP-1) and/or MAP-2 of *Rickettsia* rickettsii, and a method for protecting a host against disease or death caused by a rickettsial pathogen, including *E. canis*, by administration of such a vaccine. US Patent Application Publication No. 2004/0121433 discloses a canine ehrlichiosis vaccine, which comprises the *E. canis* immunoreactive surface protein p153, or the *E. chaffeensis* immunoreactive surface protein p156. U.S. Pat. No. 6,306,394 discloses a vaccine comprising a granulocytic ehrlichia protein or a fragment thereof, and a method of preventing ehrlichiosis in an animal by administration of such a vaccine. The aforementioned vaccines and methods are not directed to the full complement of cell surface antigens of *E. canis*, and accordingly they may not be completely effective in preventing ehrlichiosis in challenged hosts, since they offer the possibility of evasion of immune response by the infectious agent, even in vaccinated hosts.

Accordingly, there remains an unmet need in the art for an effective vaccine against *E. canis*.

*E. canis* strain Israel 611 has been propagated in vitro in a continuous canine macrophage cell line, DH82 (Keysary et al. (1996) Vet Parasitol 62:331-40). The same strain has alternately been propagated in a continuous mouse macrophage cell line, J774.A1 (Keysary et al. (2001) J Vet Diagn Invest 13(6):521-3). U.S. Pat. No. 5,192,679 discloses a method for continually growing a bacterial pathogen comprising infecting DH82 with *E. canis* and cultivating the infected cells in a suitable culture medium. The prior art does not teach or suggest an attenuated strain of *E. canis* suitable for use as a vaccine against disease caused by pathogenic strains.

SUMMARY OF THE INVENTION

The present invention provides a vaccine comprising an attenuated strain of *E. canis*, effective for prevention of ehrlichiosis in mammals, in particular, dogs and humans. The invention further provides a method for preparing an attenuated strain of *E. canis*, the method comprising serial passage of a pathogenic *E. canis* strain in tissue culture. The invention is based, in part, on the unexpected discovery that an attenuated strain of *E. canis* effectively induces protective immunity against clinical manifestation of ehrlichiosis disease in dogs, even after a single inoculation and without the use of adjuvants or other specialized reagents.

Moreover, the teachings of the present invention are advantageous over previously known vaccines and vaccination methods, since they yield a higher degree of immunity and do not require use of costly adjuvants and other specialized reagents.

In a first aspect, the invention provides an attenuated strain of *E. canis*, the strain having accession number Polish Collection of Microorganisms (PCM) B/00023, deposit date Sep. 3, 2008, hereinafter referred to as PCM B/00023. In a particular embodiment, the attenuated strain of *E. canis* has substantially the same immunizing properties as PCM B/00023. In a particular embodiment, an *E. canis* vaccine comprises (i) an effective immunizing amount of PCM B/00023, and (ii) a pharmaceutically acceptable carrier. In a particular embodiment, the *E. canis* vaccine consists essentially of (i) an effective immunizing amount of PCM B/00023, and (ii) a pharmaceutically acceptable carrier. In a particular embodiment, the *E. canis* vaccine is formulated for parenteral, oral, or intranasal administration. In a particular embodiment, the vaccine is substantially free of an adjuvant. In a particular embodiment, the *E. canis* vaccine further comprises an adjuvant. In a particular embodiment, the *E. canis* vaccine further comprises an additional active immunizing agent. In a particular embodiment, the additional active immunizing agent is an attenuated or inactivated form of a pathogen selected from the group consisting of: rabies virus; *Borrelia burgdorferi*; canine distemper virus; canine parvovirus; canine adenovirus; canine corona virus; *Giardia* spp.; *Leptospira interrogans; Babesia canis; Hepatozoon canis; Dipylidium caninum; Isospora* spp. and combinations thereof. In a particular embodiment, the PCM B/00023 is for the prevention of ehrlichiosis.

In a second aspect, the invention provides an *E. canis* vaccine, wherein the vaccine comprises (i) an effective immunizing amount of an attenuated strain of *E. canis*, and (ii) a pharmaceutically acceptable carrier. In a particular embodiment, the vaccine consists essentially of (i) an effective immunizing amount of an attenuated strain of *E. canis*, and (ii) a pharmaceutically acceptable carrier.

In a particular embodiment, the attenuated strain of *E. canis* is derived from a strain of *E. canis* selected from the group consisting of: Israel 611; Ebony; Broadfoot; Florida; Kogashima 1; Louisiana; Oklahoma; Venezuela; Sao Paulo; Jake; Demon; DJ, and Fuzzy. In a particular embodiment, the attenuated strain of *E. canis* comprises PCM B/00023. In a particular embodiment, the attenuated strain of *E. canis* consists essentially of PCM B/00023. In a particular embodiment, the attenuated strain of *E. canis* has substantially the same immunizing properties as PCM B/00023. In a particular embodiment, the attenuated strain of *E. canis* confers resistance to one or more pathogenic strains of *E. canis*. In a particular embodiment, the vaccine is formulated for parenteral, oral, or intranasal administration. In a particular embodiment, the vaccine is substantially free of an adjuvant. In a particular embodiment, the vaccine further comprises an adjuvant. In a particular embodiment, the vaccine further comprises an additional active immunizing agent. In a particular embodiment, the additional active immunizing agent is an attenuated or inactivated form of a pathogen selected from the group consisting of: rabies virus; *Borrelia burgdorferi*; canine distemper virus; canine parvovirus; canine adenovirus; canine corona virus; *Giardia* spp.; *Leptospira interrogans; Babesia canis; Hepatozoon canis; Dipylidium caninum; Isospora* spp. and combinations thereof. In another embodiment, a method of preventing ehrlichiosis in a susceptible mammalian host comprises a step of administering the vaccine of the invention to the mammalian host. In a particular embodiment, the vaccine of the invention is for the prevention of ehrlichiosis in a susceptible mammalian host.

In some embodiments, the attenuated strain of *E. canis* is one that has been serially passaged in a non-canine cell line. In a particular embodiment, the non-canine cell line is derived from a mammal selected from the group consisting of: murine, bovine, ovine, porcine, equine, feline, primate and human. In a particular embodiment, the non-canine cell line is selected from the group consisting of: J774.A1; P388D1; RAW264.7; Mm1; BDM-1, and IC-21. In a particular embodiment, the non-canine cell line is J774.A1. In a particular embodiment, the attenuated strain of *E. canis* is one that has been serially passaged in a canine cell line. In a particular embodiment, the canine cell line is selected from the group consisting of: DH82; DLC 02; MDH, and a primary cell culture of canine monocytes. In a particular embodiment, the canine cell line is DH82. In a particular embodiment, the attenuated strain of *E. canis* is one that has been serially passaged in a canine cell line and in a non-canine cell line. In a particular embodiment, the attenuated strain of *E. canis* is one that has been alternately passaged in a canine cell line and in a non-canine cell line. In a particular embodiment, the passaging in each of the canine cell line and the non-canine cell line is carried out for a number of passages of at least about 5. In a particular embodiment, the number of passages in each of the canine cell line and the non-canine cell line is about 10 to about 100. In a particular embodiment, the canine cell line is DH82, and the non-canine cell line is J774.A1. In a particular embodiment, the vaccine is substantially free of tissue culture cells.

In a third aspect, the invention provides a method of preventing ehrlichiosis in a susceptible mammalian host, the method comprising administering an effective immunizing amount of a vaccine, wherein the vaccine comprises an attenuated strain of *E. canis*, thereby preventing ehrlichiosis in said mammalian host.

In a particular embodiment, the attenuated strain of *E. canis* is derived from a strain of *E. canis* selected from the group consisting of: Israel 611; Ebony; Broadfoot; Florida; Kogashima 1; Louisiana; Oklahoma; Venezuela; Sao Paulo; Jake; Demon; DJ, and Fuzzy. In a particular embodiment, the attenuated strain of *E. canis* comprises PCM B/00023. In a particular embodiment, the attenuated strain of *E. canis* consists essentially of PCM B/00023. In a particular embodiment, the attenuated strain of *E. canis* has substantially the same immunizing properties as PCM B/00023. In a particular embodiment, the attenuated strain of *E. canis* confers resistance to one or more pathogenic strains of *E. canis*. In a particular embodiment, the administering is via a route selected from the group consisting of parenteral, oral, and intranasal administration. In a particular embodiment, the vaccine further comprises at least one pharmaceutically acceptable carrier. In a particular embodiment, the vaccine is substantially free of an adjuvant. In a particular embodiment, the vaccine further comprises an adjuvant.

In a fourth aspect, the invention provides a method for attenuating a pathogenic *E. canis* strain so as to obtain an attenuated strain of *E. canis*, the method comprising the steps of:

(i) selecting a pathogenic *E. canis* strain known to be capable of causing clinical manifestation of ehrlichiosis in a susceptible mammalian host species;

(ii) infecting a first canine cell line with the pathogenic *E. canis* strain, and thereafter serially passaging the infected first canine cell line;

(iii) infecting a non-canine cell line with the *E. canis* strain obtained from (ii), and thereafter serially passaging the infected non-canine cell line, and (iv) infecting a second canine cell line with the *E. canis* strain obtained from (iii), and thereafter serially passaging the second canine cell line. In a particular embodiment, the number of passages in steps (ii) to (iv) is sufficient to attenuate the pathogenicity of the pathogenic *E. canis* strain so as to obtain an attenuated strain of *E. canis* protective against clinical manifestation of ehrlichiosis upon administration to the susceptible mammalian host species. In a particular embodiment, the attenuated strain of *E. canis* confers resistance to one or more pathogenic strains of *E. canis*. In a particular embodiment, the serial passaging in each of steps (ii) to (iv) is carried out for a number of passages of at least about 5. In a particular embodiment, the number of passages in each of steps (ii) to (iv) is about 10 to about 100. In a particular embodiment, the method further comprises one or more additional cycles of steps (ii)-(iv), or any combination thereof. In a particular embodiment, the method further comprises an additional cycle of steps (ii) and (iii). In a particular embodiment, the additional cycle of steps (ii) and (iii) is carried out following step (iii). In a particular embodiment, the method further comprises at least one step of freezing. In a particular embodiment, the at least one step of freezing is carried out during or between any of steps (ii)-(iv). In a particular embodiment, the pathogenic *E. canis* strain is selected from the group consisting of: Israel 611; Ebony; Broadfoot; Florida; Kogashima 1; Louisiana; Oklahoma; Venezuela; Sao Paulo; Jake; Demon; DJ, and Fuzzy. In a particular embodiment, the pathogenic *E. canis* strain is Israel 611. In a particular embodiment, the first canine cell line and the second canine cell line are the same cell line. In a particular embodiment, the first canine cell line and the second canine cell line are different cell lines. In a particular embodiment, the first canine cell line and the second canine cell line are independently selected from the group consisting of: DH82; DLC 02; MDH, and a primary cell culture of canine monocytes. In a particular embodiment, the first canine cell line is DH82. In a particular embodiment, the second canine cell line is DH82. In a particular embodiment, the non-canine cell line is derived from a mammal selected from the group consisting of: murine, bovine, ovine, porcine, equine, feline, primate and human. In a particular embodiment, the mammal is murine. In a particular embodiment, the non-canine cell line is selected from the group consisting of: J774.A1; P388D1; RAW264.7; Mm1; BDM-1, and IC-21. In a particular embodiment, the first canine cell line is DH82, and the non-canine cell line is J774.A1. In a particular embodiment, the first canine cell line and the second canine cell line are DH82, and the non-canine cell line is J774.A1. In a particular embodiment, the pathogenic *E. canis* strain is Israel 611, the first canine cell line and the second canine cell line are DH82, and the non-canine cell line is J774.A1. In a particular embodiment, the method further comprises a step of preparing a suspension of the *E. canis* strain obtained from step (iv). In a particular embodiment, the step of preparing a suspension comprises centrifugation. In a particular embodiment, the suspension is a substantially cell free suspension. In a particular embodiment, the method further comprises a step of administering a sample of the *E. canis* strain obtained from step (iv) to test animals of the susceptible mammalian host species and assessing said animals for *E. canis* infection and clinical manifestation of ehrlichiosis, wherein occurrence of infection concurrent with the substantial absence of clinical manifestation of ehrlichiosis is indicative of attenuation. In a particular embodiment, the sample of the *E. canis* strain is a substantially cell free suspension. In a particular embodiment, assessing the test animals for *E. canis* infection comprises detecting *E. canis* DNA in blood samples from said test animals using PCR. In another embodiment, the method further comprises formulating the attenuated strain of *E. canis* with a pharmaceutically acceptable carrier. In another embodiment, an attenuated strain of *E. canis* is prepared by the method of the invention. In another embodiment, an ehrlichiosis vaccine comprises an attenuated strain of *E. canis* obtained by the method of the invention.

In a fifth aspect, the invention provides a method for preparing an attenuated strain of *Ehrlichia*, wherein the attenuated strain of *Ehrlichia* is protective against clinical manifestation of ehrlichiosis, the method comprising the steps of:

(i) selecting a pathogenic *Ehrlichia* strain known to be capable of causing clinical manifestation of ehrlichiosis in a susceptible mammalian host species;

(ii) infecting a first cell line derived from the susceptible mammalian host species with the pathogenic *Ehrlichia* strain, and thereafter serially passaging the infected first cell line;

(iii) infecting a cell line derived from a mammalian species other than said susceptible mammalian host species with the *Ehrlichia* strain obtained from (ii), and thereafter serially passaging the infected cell line, and (iv) infecting a second cell line derived from said susceptible mammalian host species with the *Ehrlichia* strain obtained from (iii), and thereafter serially passaging the infected second cell line. In a particular embodiment, the number of passages in steps (ii) to (iv) is sufficient to attenuate the pathogenicity of the pathogenic *Ehrlichia* strain so as to obtain an attenuated strain of *Ehrlichia* protective against clinical manifestation of ehrlichiosis upon administration to the susceptible mammalian host species. In a particular embodiment, the attenuated strain of *Ehrlichia* confers resistance to one or more pathogenic strains of *E. canis*. In a particular embodiment, the serial passaging in each of steps (ii) to (iv) is carried out for a number of passages of at least about 5. In a particular embodiment, the number of passages in each of steps (ii) to (iv) is about 10 to about 100. In a particular embodiment, the method further comprises one or more additional cycles of steps (ii)-(iv), or any combination thereof. In a particular embodiment, the method further comprises an additional cycle of steps (ii) and (iii). In a particular embodiment, the additional cycle of steps (ii) and (iii) is carried out following step (iii). In a particular embodiment, the method further comprises at least one step of freezing. In a particular embodiment, the at least one step of freezing is carried out during or between any of steps (ii)-(iv).

In a particular embodiment, the susceptible mammalian host species is selected from the group consisting of: dog, wolf, fox, jackal, deer and human. In a particular embodiment, the mammalian species other than the susceptible mammalian host species is selected from the group consisting of: dog, wolf, fox, jackal, deer and human. In a particular embodiment, the method further comprises a step of preparing a suspension of the *Ehrlichia* strain obtained from step (iv). In a particular embodiment, the step of preparing a suspension comprises centrifugation. In a particular embodiment, the suspension is a substantially cell free suspension. In a particular embodiment, the method further comprises a step of administering a sample of the *Ehrlichia* strain obtained from step (iv) to test animals of the susceptible mammalian host species and assessing said animals for *Ehrlichia* infection and clinical manifestation of ehrlichiosis, wherein occurrence of infection concurrent with the substantial absence of clinical manifestation of ehrlichiosis is indicative of attenuation. In a particular embodiment, the sample of the *Ehrlichia* strain is a substantially cell free suspension. In a particular embodiment, assessing the test animals for *Ehrlichia* infection comprises detecting *Ehrlichia* DNA in blood samples from said test animals using PCR. In a particular embodiment, the method further comprises formulating the attenuated strain of *Ehrlichia* with a pharmaceutically acceptable carrier. In another embodiment, an ehrlichiosis vaccine comprises an attenuated strain of *Ehrlichia* obtained by the method of the invention. In a particular embodiment, the method further comprises formulating the attenuated strain of *Ehrlichia* for parenteral, oral, or intranasal administration. In a particular embodiment, the pathogenic *Ehrlichia* strain is from a species selected from the group consisting of: *E. canis; E. chaffeensis; E. ewingii; E. muris*, and *E. ruminantium*.

In a sixth aspect, the invention provides an *E. canis* vaccine, wherein the vaccine comprises an effective immunizing amount of an attenuated strain of *E. canis*, and wherein the attenuated strain of *E. canis* is prepared by a method comprising the steps of:

(i) selecting a pathogenic *E. canis* strain known to be capable of causing clinical manifestation of ehrlichiosis in a susceptible mammalian host species;

(ii) infecting a first canine cell line with the pathogenic *E. canis* strain, and thereafter serially passaging the infected first canine cell line;

(iii) infecting a non-canine cell line with the *E. canis* strain obtained from (ii), and thereafter serially passaging the infected non-canine cell line, and (iv) infecting a second canine cell line with the *E. canis* strain obtained from (iii), and thereafter serially passaging the second canine cell line. In a particular embodiment, the number of passages in steps (ii) to (iv) of the method for preparing the vaccine is sufficient to attenuate the pathogenicity of said pathogenic *E. canis* strain so as to obtain an attenuated strain of *E. canis* protective against clinical manifestation of ehrlichiosis upon administration to the susceptible mammalian host species. In a particular embodiment, the attenuated strain of *E. canis* confers resistance to one or more pathogenic strains of *E. canis*. In a particular embodiment of the method for preparing the vaccine, the serial passaging in each of steps (ii) to (iv) is carried out for a number of passages of at least about 5. In a particular embodiment, the number of passages in each of steps (ii) to (iv) is about 10 to about 100. In a particular embodiment, the method for preparing the vaccine further comprises one or more additional cycles of steps (ii)-(iv), or any combination thereof. In a particular embodiment, the method further comprises an additional cycle of steps (ii) and (iii). In a particular embodiment, the additional cycle of steps (ii) and (iii) is carried out following step (iii). In a particular embodiment, the method further comprises at least one step of freezing. In a particular embodiment, the at least one step of freezing is carried out during or between any of steps (ii)-(iv). In a particular embodiment, the vaccine is formulated for parenteral, oral, or intranasal administration. In a particular embodiment, the vaccine further comprises at least one pharmaceutically acceptable carrier. In a particular embodiment, the vaccine is substantially free of an adjuvant. In a particular embodiment, the vaccine further comprises an adjuvant. Particular embodiments of the attenuated strain of *E. canis*, the pathogenic *E. canis* strain, and the canine and non-canine cell lines are as hereinbefore described.

In particular embodiments of the vaccine and methods of the invention, the susceptible mammalian host species is selected from the group consisting of: dog; wolf; fox; jackal; deer and human. In other particular embodiments of the vaccine and methods of the invention, the ehrlichiosis is caused by an organism selected from the group consisting of: *E. canis; E. chaffeensis; E. ewingii; E. muris; E. ruminantium; Anaplasma phagocytophilum; A. platys*, and *Neorickettsia risticii*.

Other objects, features and advantages of the present invention will become clear from the following description and drawings.

DETAILED DESCRIPTION OF THE INVENTION

Figure 1:
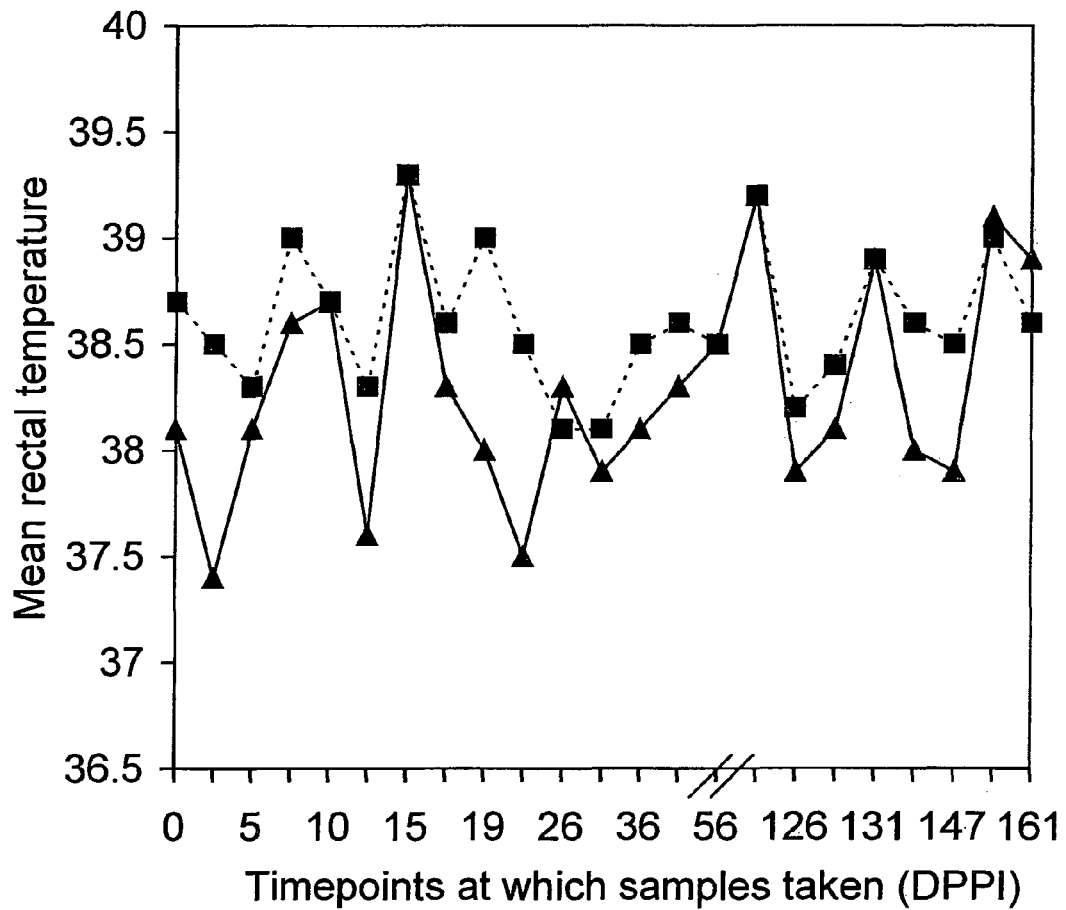
FIG. 1 illustrates mean rectal temperatures (° C.) of two dogs, referred to respectively as No. 10 (square symbols) and No. 11 (triangle symbols), experimentally infected with *E. canis*. The timepoints indicated on the x-axis are the days post primary infection (DPPI) on which samples were taken. Day 0 is the inoculation day with *E. canis*-infected DH82 cells, the *E. canis* strain obtained following serial passage in both DH82 and J774.A1 tissue culture cell lines. Day 119 is the challenge day with a virulent strain of *E. canis*.

The present invention provides an *E. canis* vaccine effective for prevention of ehrlichiosis, a potentially fatal disease which threatens both companion and wild canines, as well as humans. In humans, ehrlichiosis is often difficult to diagnose due to the non-specific nature of the symptoms, and the resultant delay in diagnosis and initiation of appropriate therapy may lead to serious complications. The invention can lead to reduction of the incidence of ehrlichiosis and its long-term consequences, and can have a positive impact on the fields of veterinary medicine and public health. The vaccine of the invention is advantageous over prior art inactivated and recombinant vaccines and related methods, since it induces a higher degree of immunity and does not require use of costly adjuvants and other specialized reagents.

Definitions

As used herein, "attenuated" refers to a live, altered form or strain of a normally pathogenic disease agent (a pathogen) which is relatively less virulent than the parent form or strain. Upon administration to a susceptible host, an attenuated strain is capable of stimulating an immune response and inducing long-term immunity, but it does not cause acute illness, although a mild sub-clinical form of the disease may occur.

As used herein, "attenuation", "attenuating" and related grammatical forms refer to procedures that render a pathogen attenuated, such as repeated passage in tissue culture. The process of attenuation may result from an accumulation of point mutations or recombination events which result in a reduction of the virulence of the pathogen. Accordingly, an "attenuated vaccine" refers to a vaccine comprising an attenuated strain. An attenuated strain and a vaccine comprising an attenuated strain induce strong humoral and cell-mediated immune responses, and generally only one or two immunizations are required to induce long-term immunity to the pathogen.

Accordingly, an attenuated strain is said to be "derived from" a named pathogenic parent strain, when the starting material for the attenuation process was that pathogenic strain.

It is to be explicitly understood that an attenuated strain and a vaccine prepared therefrom are distinct and different from an inactivated strain and a vaccine prepared therefrom, since the latter are killed and non-infectious, and are produced using means which are intended to kill the pathogen, such as chemical agents, heat or UV light. In general, an inactivated strain and a vaccine prepared therefrom are relatively weaker than the corresponding attenuated forms, since the immunity induced by inactivated strains and vaccines is mostly humoral and short-lived. Accordingly, inactivated vaccines generally require use of adjuvants, as well as multiple immunizations.

The terms "pathogenic" and "virulent" are used interchangeably herein to describe an organism or a strain thereof which causes disease (i.e. a pathogen) in a susceptible host, for example *E. canis* and related ehrlichial species which cause ehrlichiosis in canines and humans.

The terms "pathogenicity" and "virulence" are used interchangeably herein to refer to the ability and/or relative ability of a pathogen to cause disease in a susceptible host.

As used herein, the term "infectivity in a susceptible mammalian host species" refers to the ability of an organism to penetrate target cells of a susceptible mammalian host species. For example, *E. canis* and related ehrlichial species have infectivity for macrophages and monocytes of canines and other mammals. It is to be understood however, that infectivity of a particular species and strain of ehrlichiae does not necessarily lead to clinical manifestation of disease, i.e. ehrlichiosis, in a particular host. Whether or not clinical manifestation of ehrlichiosis occurs is apparently dependent on a number of factors, including the species and strain of the ehrlichiae, the expression of particular virulence factors by the ehrlichiae, and the immune status and genetic makeup of the host.

As used herein, the term "effective immunizing amount" refers to that amount of a vaccine or of an attenuated *Ehrlichia* strain according to the invention which is sufficient to be protective against clinical manifestation of ehrlichiosis in a susceptible mammalian host.

As used herein, the term "confers resistance to one or more pathogenic strains" refers to the ability of an agent i.e. an attenuated strain in the context of the present invention, to protect a host against the virulent effects of infection with or exposure to such a pathogenic strain.

The term "ehrlichiae" is used herein generically to refer to members of the family Anaplasmatacea such as those of the genera *Ehrlichia, Anaplasma*, and *Neorickettsia*. Such members include for example, *Ehrlichia canis, Anaplasma* (formerly *Ehrlichia*) *phagocytophilum*, and *Neorickettsia* (formerly *Ehrlichia*) *sennetsu*. The term is also used herein to refer to a multiplicity of organisms of any particular species and strain of the aforementioned family. Similarly, the term "ehrlichial" is used herein to describe diseases, organisms, immunological responses and other medical and veterinary terms and events associated with and/or caused by members of the family Anaplasmatacea.

As used herein, the singular forms "a", "an" and "the" include plural forms unless the context clearly dictates otherwise. Thus, for example, reference to "an attenuated strain" includes combinations of attenuated strains, and so on.

*E. canis*, Strains Thereof, and Related Organisms

*Ehrlichia canis*, a member of the order Rickettsiales, is a tick-borne obligate intracellular, gram negative, dimorphic bacterium that resides as a microcolony within a membrane-lined intracellular vacuole (morula), primarily in monocytes and macrophages of mammalian hosts, particularly canines. Each morula may contain 100 or more organisms. Ultrastructurally, *E. canis* has two forms, termed reticulate and dense-cored cells, resembling morphologically similar reticulate and elementary body forms of chlamydiae. Ehrlichiae have relatively small genomes (~1.2 Mbp) and do not possess extrachromosomal plasmids. Members of the genus *Ehrlichia* include *E. canis, E. chaffeensis, E. ewingii, E. muris* and *E. ruminantium*. Phylogenetic analysis of 16S ribosomal DNA (rDNA) and groEL genes of *E. canis* and *E. chaffeensis* support the close genetic relatedness of these organisms, and, considerable antigenic cross reactivity between them has been reported (Chen et al. (1997) Clin Diag Lab Immunol 4: 731-735; Chen et al. (1994) Am J Trop Med Hyg 50: 52-58; Rikihisa et al. (1994) J Clin Microbiol 32: 2107-12).

Ehrlichiae have a complex life cycle involving a tick vector and a mammalian host and have developed strategies to establish persistent infections in the natural hosts. *E. canis* is transmitted between dogs by the brown dog tick *Rhipicephalus sanguineus* and is maintained in nature by persistent infection of both wild and domestic dogs. Nymphal or larval ticks typically are infected with *E. canis* by feeding on a persistently infected dog, and maintain the infection transtadially as the tick molts from stage to stage. Other mammalian species, namely wolf, fox, jackal and deer, may also be reservoirs for *E. canis*.

The genus *Ehrlichia* is closely related to the genera of *Anaplasma* and *Neorickettsia*, whose members have a similar intracellular life cycle. The organisms *Anaplasma phagocytophilum, A. platys* and *Neorickettsia risticii* were formerly classified in the genus *Ehrlichia*, but have been reclassified on the basis of phylogenetic analysis of 16S rDNA.

The mechanism of persistent ehrlichial infection is unclear, although immunoreactive proteins and potential pathogenic mechanisms have been identified. Members of the genus *Ehrlichia* have a multigene family encoding homologous, but distinct, major surface proteins. A multigene loci of *E. canis* includes 25 paralogous genes encoding 28 kDa proteins that may be differentially expressed in the tick and mammalian hosts. Furthermore, two large molecular weight glycoproteins have been identified in *E. canis* (gp140 and gp200) and the corresponding orthologs in *E. chaffeensis*. These glycoproteins appear to be important targets of the host immune response and elicit a strong antibody response.

In a currently preferred embodiment, the attenuated strain of *E. canis* according to the invention is that having accession number Polish Collection of Microorganisms (PCM) B/00023, deposit date Sep. 3, 2008 (referred to herein as PCM B/00023) which was derived from strain Israel 611. An exemplary attenuation procedure, such as that used to develop PCM B/00023, is described herein in Example 1. The efficacy of an attenuated strain prepared in the same manner for the prevention of clinical manifestation of ehrlichiosis in experimentally infected animals is described herein in Example 2.

The present invention further encompasses an attenuated strain of *E. canis* which has substantially the same immunizing properties as PCM B/00023. The term "immunizing properties" includes, but is not limited to one or more of: the ability to induce humoral and cell-mediated immune responses; the titer and duration of such responses; the ability to induce such responses in the absence of adjuvant; the ability to induce long-term immunity; the ability to confer protection against clinical manifestation of disease i.e. ehrlichiosis, and the ability to confer resistance to a pathogenic strain or organism.

A pathogenic *E. canis* strain which may be used for preparation of the attenuated strain and vaccine of the invention may be selected from any known strain or isolate, including but not limited to Israel 611, Ebony, Broadfoot, Florida, Kogashima 1, Louisiana, Oklahoma, Venezuela, Sao Paulo, North Carolina State University (NCSU) strain Jake, and NCSU isolates Demon, DJ and Fuzzy. Furthermore, a suitable pathogenic *E. canis* strain may be one that has been serially passaged in a cell line, such as the canine cell line DH82.

The strain Israel 611 was previously disclosed by some of the inventors of the present invention, and has two forms of morulae: (1) tightly packed and (2) loosely packed, and its 16S rRNA gene sequence is three nucleotides different than the Oklahoma strain and four nucleotides different than the Florida strain, with a gap of one nucleotide in each (Keysary et al. (1996) Vet Parasitol 62:331-40; Keysary et al. (2001) Vet Diagn Invest 13(6):521-3). The degree of homology difference from the Oklahoma strain is 0.54 percent while the difference from the Florida strain is 0.61 percent (Keysary, 1996, supra).

The Ebony strain is reportedly 99.9 percent homologous with the Oklahoma strain based on the 16S rDNA sequence (Mathew et al. (1996) Am J Vet Res 57(11):1594-8). Ebony has been shown to be transmissible to dogs by nymphal and adult brown dog tick (*Rhipicephalus sanguineus*).

The Florida strain is disclosed in U.S. Pat. No. 6,458,942 and U.S. Pat. No. 6,432,649, and reportedly contains a conserved major immunoreactive 28-kDa protein gene (U.S. Pat. No. 6,458,942) and a p30 gene belonging to the omp-1 multiple gene family (U.S. Pat. No. 6,432,649). Moreover, U.S. Pat. No. 6,043,085 discloses that the Florida strain has a 120 kDa immunodominant antigenic protein, containing 14 repeats with 36 amino acids each, which are predicted to be surface-exposed. The repeat units are hydrophilic that form the core of the surface exposed regions of the protein, and are rich in serine and glutamic acid. Serine and glutamic acid each comprise 19% of the amino acids of a repeat unit. The Florida strain is postulated to be less virulent than the *E. canis* strain Jake (Breitschwerdt et al. (1998) Antimicrobial Agents and Chemotherapy 42(2):362-68), while serological comparison with the Oklahoma strain revealed 100% specificity and 87.5% sensitivity (Dawson et al. (1991) J Infect Dis. March; 163(3):564-71).

Like the Florida strain, the Louisiana strain has a conserved major immunoreactive 28-kDa protein gene (U.S. Pat. No. 6,458,942), a p30 gene belonging to the omp-1 multiple gene family (U.S. Pat. No. 6,432,649), and, as disclosed in U.S. Pat. No. 6,043,085, a 120 kDa immunodominant antigenic protein, containing 14 repeats with 36 amino acids each, which are predicted to be surface-exposed. The repeat units are hydrophilic that form the core of the surface exposed regions of the protein, and are rich in serine and glutamic acid. Serine and glutamic acid each comprise 19% of the amino acids of a repeat unit.

Similarly, the Oklahoma strain has a conserved major immunoreactive 28 kDa protein gene (U.S. Pat. No. 6,458,942), a p30 gene belonging to the omp-1 multiple gene family (U.S. Pat. No. 6,432,649), and, as disclosed in U.S. Pat. No. 6,043,085, a 120 kDa immunodominant antigenic protein, containing 14 repeats with 36 amino acids each, which are predicted to be surface-exposed. The repeat units are hydrophilic that form the core of the surface exposed regions of the protein, and are rich in serine and glutamic acid. Serine and glutamic acid each comprise 19% of the amino acids of a repeat unit. Additionally, McBride et al. disclose that Oklahoma possesses a glycoprotein gene (2,064 bp) that encodes proteins of 548 to 688 amino acids with predicted molecular masses of only 61 and 73 kDa, but with electrophoretic mobilities of 140 kDa (P140), respectively (McBride et al. (2000) Infection and Immunity 68(1):13-18). The 140 kDa protein gene has fourteen nearly identical, tandemly arranged 108 bp repeat units. The 14-repeat region (78%) of the P140 gene (1,620 bp) was expressed in *E. coli*, and the recombinant protein exhibited molecular masses ranging from 1.6 to 2 times larger than those predicted by the amino acid sequences. Antibodies against the recombinant proteins react with *E. canis* P140. Carbohydrate was detected on the *E. canis* recombinant proteins. A carbohydrate compositional analysis identified glucose, galactose, and xylose on the recombinant proteins. The presence of only one site for N-linked (Asn-Xaa-Ser/Thr) glycosylation, a lack of effect of N-glycosidase F, the presence of 70 and 126 Ser/Thr glycosylation sites in the repeat regions of P120 and P140, respectively, and a high molar ratio of carbohydrate to protein suggest that the glycans may be O-linked (McBride et al. (2000) Infection and Immunity 68(1):13-18). Oklahoma can be grown in the canine macrophage cell line DH82 in minimum essential medium containing 12.5% fetal bovine serum and 200 mM L-glutamine (Bowie et al. (1999) Clin. Diagnostic Lab. Immun.6(2):209-15). A serological comparison with Florida strain revealed 100% specificity and 87.5% sensitivity (Dawson 1991, supra). Similarity of 99.9 percent, based on the 16S rDNA sequence, has been found with the strains Ebony (Mathew 1996), Kagoshima 1 (Unver et al. (2003) Ann NY Acad. Sci. 990:692-8), and Venezuela (Unver et al. (2001) J Clin Microbiol. 39(8):2788-93).

The NCSU isolates Demon, DJ and Fuzzy, and the NCSU strain Jake, all possess a conserved major immunoreactive 28 kDa protein gene (U.S. Pat. No. 6,458,942). It has been disclosed that DJ, Fuzzy and Jake also have a p30 gene belonging to the omp-1 multiple gene family (U.S. Pat. No. 6,432,649). Jake is believed to be more virulent than the Florida strain (Breitschwerdt 1998, supra).

Nearly the entire 16S rRNA sequence of Kagoshima 1 was found to be most similar to the sequences from Oklahoma and Venezuela *E. canis* strains (1 base pair difference out of 1,387) with a 99.9 percent sequence identity (Unver 2003, supra). In addition, and similarly, to its high sequence identity to the Kagoshima 1 strain, the Venezuela strain is 99.9 percent similar to the Oklahoma strain based on the 16S rDNA sequence (Unver 2001, supra).

Pathogenicity of *E. canis* and Ehrlichiosis

The selected *E. canis* strain may be deemed to be pathogenic on the basis of its isolation from a mammalian host exhibiting clinical signs and/or symptoms of ehrlichiosis, or alternately or in addition, on the basis of its ability to cause clinical signs and/or symptoms of ehrlichiosis upon administration to a mammalian host, for example in an experimental infection. Such means of determining pathogenicity are known to those of skill in the art.

The pathogenic *E. canis* strain may be from a clinical isolate, an *E. canis* infected cell culture or an *E. canis* stock passaged in live animals, for example dogs. A clinical isolate may be a sample from blood, bone marrow, spleen, saliva, or isolated fractions thereof. A cell culture is conveniently a continuous cell culture, for example the canine macrophage cell line DH82, disclosed in Dawson et al (1991) J Infect Dis 163:564-567 and in Wellman et al (1988) In Vitro Cell Develop Biol 24:223-228. A cell culture may however, be a primary culture of peripheral blood monocytes, as disclosed in Nyindo et al. (1971) Am J Vet Res 32:1651-1658, or of monocytes, as disclosed in Hemelt et al. (1980) Cornell Vet 70:37-42. Other possible cell culture methods may utilize canine peritoneal macrophages, as disclosed in Stephenson et al (1977) Am J Vet Res 38:1815-1819; human-canine hybrid cells (Stephenson et al (1977), supra), or a human microvascular endothelial cell line, as disclosed in Dawson et al (1993) Pathobiology 61: 293-296. An *E. canis* stock passaged in live animals may be obtained as disclosed in US Patent Application Publication Nos. 2005/0202046 and 2006/0188524.

Ehrlichiosis refers to the tick-transmitted disease which occurs in canines (domestic and wild), wolves, foxes, jackals, deer and humans, and which may be caused by any of a number of related *Ehrlichia* species, including *E. canis, E. chaffeensis, E. ewingii, E. muris*, and *E. ruminantium*. Ehrlichiosis may also be caused by *Anaplasma* (formerly *Ehrlichia*) *phagocytophilum, A. platys* and *Neorickettsia* (formerly *Ehrlichia*) *sennetsu* and *A. platys*. These organisms may have different host cell tropisms including monocytes, granulocytes, and platelets. Ehrlichiosis in canines is termed canine monocytic ehrlichiosis (CME) and is predominantly caused by *E. canis*, although it may also be caused by *E. chaffeensis*. Ehrlichiosis in humans has been termed human monocytic ehrlichiosis (HME) and Venezuela Human Ehrlichiosis (VHE), which have been determined to be caused by *E. chaffeensis* and *E. canis*, respectively.

Susceptible mammalian hosts for ehrlichiosis include the aforementioned mammals, as well as additional species including cows, horses, cats, swine, rodents and sheep.

*E. canis* infections in dogs are characterized by acute and subclinical stages, and in some cases, a chronic stage. In the acute stage of the disease, dogs may resolve the disease, but develop subclinical persistent infections, and thus, become asymptomatic carriers of the infection. When the chronic form of the disease occurs, the response to antibiotic therapy may be poor and dogs often die from hemorrhage, severe debilitation or secondary infection.

Clinical manifestation of ehrlichiosis in dogs is characterized by signs including fever; anorexia; petechiae; ecchymoses, epistaxis, lymphadenopathy; leucopenia; thrombocytopenia; reticuloendothelial hyperplasia; hyperglobulinemia; myalgia; mucopurulent ocular and nasal discharge; splenomegaly, and combinations thereof. In humans, clinical manifestation of ehrlichiosis is characterized by symptoms including fever, headache, myalgia, rash, nausea/vomiting, altered mental status, lymphadenopathy, thrombocytopenia, elevated hepatic transaminases, hypoalbuminemia, lymphopenia, leucopenia, hyponatremia and combinations thereof.

Clinical manifestation of ehrlichiosis may be accompanied by replication of ehrlichiae in the host. The presence of ehrlichial DNA in affected hosts may be detected by analysis of body fluid or tissue samples taken from the host e.g. blood, using a polymerase chain reaction (PCR) technique. The PCR technique may conveniently employ primers directed to nucleic acid sequences corresponding to major surface proteins of ehrlichiae, for example, p30, p43 and map2 of *E. canis*, and p28, p120 and map2 of *E. chaffeensis*, as described for example, in Harrus et al. (1998) J Clin Microbiol 36(1): 73-76; Ohashi et al. (1998) J Clin Microbiol 36(9):2671-2680; Yu et al. (2000) J Clin Microbiol 38(1):369-374; McBride et al. (2001) J Clin Microbiol 39(1): 315-322; Stich et al (2002) J Clin Microbiol 40(2):540-546, and Knowles et al (2003) Clin Diagn Lab Immunol 10(4):520-524.

Methods of Attenuation

The invention provides a method for attenuating a pathogenic *E. canis* strain, and a method for preparing an attenuated strain of *Ehrlichia*. The methods comprise the steps of: (i) selecting a pathogenic *E. canis* or *Ehrlichia* strain known to have infectivity in a susceptible mammalian host species and to be capable of causing clinical manifestation of ehrlichiosis in the susceptible mammalian host species; (ii) infecting a first tissue culture cell line with the pathogenic *E. canis* or *Ehrlichia* strain and thereafter serially passaging the infected first tissue culture cell line, and (iii) infecting a second tissue culture cell line with the strain obtained from (ii), and thereafter serially passaging the infected second tissue culture cell line. In a particular embodiment, the first tissue culture cell line is a canine cell line, and the second tissue culture cell line is a non-canine mammalian cell line. In another embodiment, the first tissue culture cell line is a first cell line derived from the susceptible mammalian host species, and the second tissue culture cell line is derived from a mammalian species other than the susceptible mammalian host species.

The methods further comprise an additional step, namely step (iv), in which one embodiment comprises infecting a second canine tissue culture cell line with the strain obtained from (iii) and thereafter serially passaging the infected second canine tissue culture cell line. This embodiment is employed when the first tissue culture cell line in step (ii) is a canine cell line, and the second tissue culture cell line in step (iii) is a non-canine mammalian cell line.

In another embodiment, step (iv) comprises infecting a second cell line derived from the susceptible mammalian host species with the strain obtained from (iii) and thereafter serially passaging the infected second cell line derived from the susceptible mammalian host species.

It is to be explicitly understood that the tissue culture cell lines used in steps (ii) and (iii) are to be derived from different mammalian species. The tissue culture cell line used in step (iv) must be derived from the same mammalian species as that of the cell line of step (ii), although it does not have to be the identical cell line. That is, the cell line used in step (iv) may be the same or different from that used in step (ii), but when it is different, the cell line of step (iv) is to be derived from the same mammalian species as that from which the cell line of step (ii) is derived. In some embodiments, the cell lines used in steps (ii) and (iv) are different, but they are derived from the same mammalian species.

For example, a dog monocyte cell line may be used in step (ii), such as DH82, and a murine monocyte cell line may be used in step (iii), since these cell lines are derived from different mammalian species. The cell line used for step (iv) must be derived from dog tissue. According to one embodiment, it may be DH82 i.e. identical to the cell line of step (ii). In other embodiments, the cell line used for step (iv) will be a different dog cell line, although it may be derived from hematopoietic cells, or any other lineage, tissue or compartment originating in dog.

In some embodiments, the cell line used in steps (ii) and (iv) is a canine tissue culture cell line. Examples of suitable canine cell lines include, but are not limited to DH82, DLC 02, MDH, and a primary cell culture of canine monocytes. A currently preferred canine tissue culture cell line is the canine monocyte DH82 cell line.

It is to be understood however, that non-canine mammalian cell lines may be used in steps (ii) and (iv), in which case, a canine cell line may be used in step (iii).

In some embodiments, the cell line used in step (iv) is a non-canine mammalian tissue culture cell line.

Non-canine mammalian species include murine, bovine, ovine, porcine, equine, feline, primate and human. Examples of a suitable non-canine mammalian tissue culture cell line include, but are not limited to J774.A1; P388D1; RAW264.7; Mm1; BDM-1, and IC-21. A currently preferred second tissue culture cell line is the murine monocyte cell line J774.A1.

A suitable combination of a first tissue culture cell line for step (ii) and a second tissue culture cell line for step (iii) is DH82 and J774.A1, respectively. An example of a suitable pathogenic *E. canis* strain to be used for serial growth and attenuation in these strains is Israel 611. Other pathogenic *E. canis* strains, hereinbefore described, may be used.

Susceptible mammalian host species are those which have the potential to develop ehrlichiosis upon infection with ehrlichiae. Susceptible mammalian host species include dog, wolf, fox, jackal, deer and human.

In some embodiments, the cell lines used in steps (ii) to (iv) are all hematopoietic cell lines, which may be advantageous due to the tropism of *Ehrlichia* species. In other embodiments, some of the cell lines may be derived from non-hematopoietic cell or tissues.

In a particular embodiment, the method further comprises one or more additional cycles of steps (ii)-(iv), or any combination thereof. That is, any of steps (ii)-(iv) may be repeated subsequently to a previous step. For example, steps (ii) and (iii) may be repeated in sequence after step (iii) is initially carried out. In another embodiment, steps (ii) and (iii) may be repeated in sequence after step (iv). In a particular embodiment, the method further comprises an additional cycle of steps (ii) and (iii). In a particular embodiment, the additional cycle of steps (ii) and (iii) is carried out following step (iii).

Infecting refers to the practice of introducing a strain of *E. canis* or a different *Ehrlichia* to a particular tissue culture cell line, in the presence of a suitable growth medium, and under suitable conditions e.g. of temperature, humidity and carbon dioxide, for a period of time sufficient to achieve infection of at least a proportion of the cells in culture. Infection of the cells may be detected by known means, such as immunofluorescence and electron microscopy, as disclosed for example, in Keysary et al. (2001), supra. Other means of detecting infection are known to those of skill in the art.

Passaging refers to the practice of transferring a portion of infected cells in tissue culture to a different growth vessel containing uninfected cells and fresh medium. Passaging is the standard means by which an organism which grows in a host cell may be propagated. Serial passaging refers to the practice of continuously repeating the passaging process, usually at defined intervals, or at endpoints defined by a particular stage of cell growth or infection. For example, tissue culture cells infected with *E. canis* may be passaged every 7 to 14 days, or when at least 80% of the cells are infected. Other time intervals or endpoints are also suitable, for example, passage every 10 to 30 days, or when 90 to 100% of the cells are infected. The time interval chosen between passages will depend on the infection rate of the cells. It is to be explicitly understood, that the term "passaging" may refer to both the initial stage of infecting the cells, as well as the subsequent stage of growth within the cells. The infection stage may require a longer period of time than the growth stage.

In accordance with the methods of the invention, the ehrlichiae may be alternately passaged in different tissue culture cell lines, which are termed herein (a) and (b) for the purpose of explanation. "Alternately passaging" refers to the process of propagating the ehrlichiae first in tissue culture cell line (a) and then in tissue culture cell line (b), wherein each propagation step may involve a single passage or serial passaging using a number of passages, for example, at least about 5, such as about 10 or about 50 or about 100.

Media which are suitable for infection and passaging in tissue culture cell lines include for example, RPMI-1640, OPTI-MEM (Reduced Serum Media, a modification of Eagle's Minimum Essential Media), AIM V (Serum Free Medium) and Dulbecco's Modified Eagle's Medium (DMEM). A growth medium may be supplemented variously with serum (e.g, fetal calf serum, fetal bovine serum, horse serum), glucose, salts, amino acids and antibiotics, as is known in the art.

A suspension of *E. canis* may be obtained from the tissue culture cell line in which it is propagated. The suspension may be cell free or substantially cell free. A suitable method comprises disruption of the infected cells by homogenization or sonication, followed by centrifugation. The method may involve repeated rounds of cell disruption and centrifugation, and may further involve size exclusion chromatography. The centrifugation may be density gradient centrifugation. Suitable methods are described for example, in Keysary et al. (2001), supra; McBride et al. (2001), supra; Knowles et al. (2003), supra and Rikihisa (1991) J Clin Microbiol 29(9): 2024-2029. An *E. canis* suspension thus obtained may be used to infect a non-infected culture of the same cell line, or a non-infected culture of a different cell line. The suspension may further be tested in an experimental animal system to determine if the *E. canis* therein has become attenuated. If the *E. canis* strain is attenuated, the suspension may be used to prepare an attenuated vaccine.

The methods disclosed herein provide an attenuated strain of *E. canis* (or *Ehrlichia*) which confers resistance to one or more pathogenic strains of *E. canis*, as demonstrated by Example 2.

The number of passages in steps (ii) to (iv) of the subject methods may be sufficient to attenuate the pathogenicity of the pathogenic *E. canis* strain (or other *Ehrlichia*) so as to obtain an attenuated strain of *E. canis* (or other *Ehrlichia*) protective against clinical manifestation of ehrlichiosis. It is to be understood that there is no particular upper or lower limit to the number of passages for any of these individual steps, and the particular number of passages or range thereof for each step may vary according to the *Ehrlichia* species and strain used, as well as the particular tissue culture cell types. However, it is well within the ability of one of average skill in the art to determine the required number, for example by using a matrix experimental design, wherein the number of passages in each step is varied.

In particular embodiments of the methods disclosed herein, the serial passaging in each of steps (ii) to (iv) is carried out for a number of passages of at least about 5. In particular embodiments, the number of passages in each of steps (ii) to (iv) is at least about 5, for example about 10 to about 100. In other particular embodiments, the number of passages in each of steps (ii) to (iv) is about 50. In a particular embodiment, the number of passages in step (iii) is about equal to the number of passages in step (ii), for example about 50 each. In a particular embodiment, the number of passages in step (iii) is about twice the number of passages in step (ii), for example about 100 in step (iii) and about 50 in step (ii). Depending on the time interval between passages, passaging the infected tissue culture cell lines in each of steps (ii)-(iv) may be for a period of about 1 year. In particular embodiments, passaging the infected tissue culture cell lines in each of steps (ii)-(iv) is for a period of about 1 year to about 5 years, for example, about 2 years to about 4 years.

In alternate embodiments, the methods of the invention further comprise one or more additional cycles of steps (ii)-(iv), or any combination thereof. In particular embodiments, the method comprises an additional cycle of steps (ii) and (iii), wherein the additional cycle is carried out following step (iii).

When such an additional cycle of steps (ii) and (iii) is included, the number of passages in each of steps (ii) and (iii) may be from about 5 to about 50, for example, from about 10 to about 20. In this additional cycle, the passaging in each of steps (ii) and (iii) may be for a period of at least one month, for example, about 2 months to about 6 months.

The method may further comprise at least one step of freezing. The freezing may be carried out during or between any of steps (ii)-(iv). The freezing may comprise short or long term storage at −20° C. or −70° C. as is known in the art.

To determine if a pathogenic *E. canis* strain has become attenuated upon repeated serial passage in tissue culture upon practice of the method of the invention, a sample preparation of ehrlichiae infected tissue culture cells, or a substantially cellfree suspension of ehrlichiae prepared from tissue culture as hereinbefore described, is administered to test animals in an experimental infection system to assess pathogenicity of the ehrlichiae in the sample.

An experimental infection system typically employs a number of healthy middle aged dogs who are vaccinated for standard canine diseases, including distemper virus, parvovirus, parainfluenza, adenovirus-2, *Leptospira* spp. and rabies. At the time of infection, the dogs should be seronegative for *E. canis* antibodies, as determined by the indirect immunofluorescence antibody (IFA) assay, and no ehrlichial DNA should be detected in blood samples using PCR using specific primers for *E. canis*. Hematological and clinical chemistry parameters should be within the normal reference range, and the study should be conducted in a tick free animal facility.

Following inoculation of *E. canis* or *E. canis* infected cells to the test dogs, daily physical examination should be conducted for an appropriate period e.g. 4 weeks, to detect clinical signs of erhlichiosis. Blood samples should be drawn at different intervals following inoculation and evaluated for antibodies against *E. canis*, for example by IFA, as disclosed in Keysary et al (1996), supra, and/or for *E. canis* DNA using PCR amplification, as disclosed for example in Stich et al (2002), supra.

Attenuation is strongly suggested if no clinical manifestation of ehrlichiosis is observed, or if only mild signs of disease are observed, yet infection is confirmed by IgG seroconversion and positive PCR.

The ability of an attenuated *E. canis* strain to confer protection against ehrlichiosis in a susceptible mammalian host may be determined by challenge infection of test dogs who have been administered an attenuated *E. canis* strain, as described above, in parallel with challenge infection of control dogs who have not been exposed to or administered the attenuated *E. canis* strain. Test and control dogs should be PCR negative at the time of challenge. A challenge stock should contain pathogenic *E. canis*, for example blood from a dog confirmed to have ehrlichiosis according to clinical signs and positive PCR. A challenge stock may be prepared from repeatedly passage in live hosts, as disclosed in US Patent Application Publication Nos. 2005/0202046 and 2006/0188524. Protection is strongly suggested if no clinical manifestation of ehrlichiosis is observed in the test dogs, or if only mild signs of disease are observed, while the control dogs develop clinical and hematological signs consistent with ehrlichiosis. Protection is confirmed in the test dogs upon positive PCR, which indicates occurrence of infection concurrent with a substantial absence of clinical manifestation of ehrlichiosis.

It is to be understood that the attenuated *E. canis* strain and vaccine of the invention may be protective against clinical manifestation of ehrlichiosis, even when the ehrlichiosis is caused by ehrlichial species other than *E. canis*. That is, it may be protective against ehrlichiosis caused by any of *E. canis, E. chaffeensis, E. ewingii, E. muris, E. ruminantium, Anaplasma phagocytophilum, A. platys,* and *Neorickettsia risticii*. Furthermore, the attenuated *E. canis* strain and vaccine of the invention may be suitable for administration to more than one type of mammalian host species, including dogs and humans.

Vaccines

The invention further provides an *E. canis* vaccine, wherein the vaccine comprises (i) an effective immunizing amount of an attenuated strain of *E. canis*, and (ii) a pharmaceutically acceptable carrier. The inventors of the present invention have found that an attenuated *E. canis* strain may be obtained by sequential growth and serial passage of a pathogenic *E. canis* strain in at least two different types of tissue culture cell lines, derived respectively from a canine mammalian species and a non-canine mammalian species, as described herein. The number of serial passages in cell culture may be sufficient to attenuate the pathogenicity of the pathogenic *E. canis* strain. Importantly, the attenuated strain of *E. canis* confers resistance to one or more pathogenic strains of *E. canis* upon infection of a susceptible host with such a pathogenic strain, such that the host remains substantially free of clinical disease.

In a currently preferred embodiment, the vaccine comprises the attenuated *E. canis* strain having accession number Polish Collection of Microorganisms (PCM) B/00023, deposit date Sep. 3, 2008 (PCM B/00023). In a particular embodiment, the vaccine consists essentially of (i) an effective immunizing amount of PCM B/00023, and (ii) a pharmaceutically acceptable carrier. In alternate embodiments, the vaccine comprises an attenuated strain of *E. canis* which has substantially the same immunizing properties as PCM B/00023.

It is generally preferable that the vaccine be substantially free of cells from originating from any of the tissue culture cell lines in which the attenuated strain was prepared and propagated.

An effective immunizing amount means that amount determined to be protective against clinical manifestation of ehrlichiosis in a susceptible mammalian host. The effective amount may vary according on the route of administration. The effective immunizing amount may further vary according to the weight and type of mammal being immunized. For example, small, medium and large breed dogs will require different doses which are calculated according to body weight, as is known in the field of veterinary medicine. An effective amount to be administered may be readily determined by one of skill in the art.

An effective immunizing amount may be expressed in various units, or calculated by different means. For example, the effective immunizing amount may be expressed in terms of the number of attenuated ehrlichiae per unit dose. In this case, an effective immunizing amount may be within the range of $1 \times 10^3$ to $1 \times 10^{12}$ attenuated ehrlichiae per unit dose. In particular embodiments, an effective immunizing amount may be $1 \times 10^3$, or $1 \times 10^4$, or $1 \times 10^5$, or $1 \times 10^6$ or $1 \times 10^7$ or $1 \times 10^8$ or $1 \times 10^9$, or $1 \times 10^{10}$, or $1 \times 10^{11}$, or $1 \times 10^{12}$ attenuated ehrlichiae per unit dose. Alternately, the effective immunizing amount may be expressed as micrograms of ehrlichiae protein per kg body weight. In this case, an effective immunizing amount may be in the range of 1 to 100 micrograms ehrlichiae protein per kg body weight per unit dose. Alternately, an effective immunizing amount may be expressed in terms of ehrlichiae-infected tissue culture cells. In this case, an effective immunizing amount may be in the range of $1 \times 10^3$ to $1 \times 10^{12}$ tissue culture cells, wherein 40-100% of the cells are infected. Alternately, the effective immunizing amount may be expressed in tissue culture infective dose units (TCID$_{50}$), meaning the amount of ehrlichiae sufficient to infect half the cells in a tissue culture. In this case, the effective immunizing amount may be in the range of $1 \times 10^3$ to $1 \times 10^{12}$ TCID$_{50}$ attenuated *E. canis* per unit dose.

The attenuated strain of *E. canis* may be derived from any strain of *E. canis*, such as for example, Israel 611; Ebony; Broadfoot; Florida; Kogashima 1; Louisiana; Oklahoma; Venezuela; Sao Paulo; Jake; Demon; DJ, and Fuzzy. The attenuated strain of *E. canis* may be one that has been serially passaged in a non-canine cell line. The non-canine cell line may be derived from a mammal, including that classified as murine, bovine, ovine, porcine, equine, feline, primate and human. The non-canine cell line may be selected from J774.A1; P388D1; RAW264.7; Mm1; BDM-1, and IC-21. The aforementioned cell lines are murine hematopoietic cell lines. Non-canine cell lines include those derived from any other mammal and from any non-hematopoietic lineage thereof. In a particular embodiment, the non-canine cell line is the murine monocyte cell line J774.A1.

The attenuated strain of *E. canis* may be one that has been serially passaged in a canine cell line. The canine cell line may be selected from the group consisting of: DH82; DLC 02; MDH, and a primary cell culture of canine monocytes. In a particular embodiment, the canine cell line is DH82.

The attenuated strain of *E. canis* may be one that has been serially passaged in a canine cell line and in a non-canine cell line. In one particular embodiment, the canine cell line is DH82, and the non-canine cell line is J774.A1.

In a particular embodiment, the attenuated strain of *E. canis* may be one that has been alternately passaged in a canine cell line and in a non-canine cell line. The number of passages in each of the canine cell line and the non-canine cell line may be at least about 5, for example about 10 to about 100.

The vaccine may be formulated for parenteral, oral, or intranasal administration. Parenteral administration includes intramuscular, intraperitoneal, subcutaneous, intradermal and intravenous routes of administration. Parenteral administration forms include sterile liquid forms such as solutions or suspensions.

Oral administration forms include capsules, tablets, chewable tablets, liquid solutions, suspensions, powders or elixirs for oral administration.

Any inert carrier may be used, such as saline, phosphate-buffered saline, or any such carrier in which the vaccine has suitable solubility properties. The vaccines may be in the form of single dose preparations or in multi-dose flasks which can be used for mass vaccination programs.

The vaccine may be substantially free of an adjuvant, or agents which provide the effects of an adjuvant. Alternately, the vaccine may comprise an adjuvant for enhancing production of antibodies and/or immune cells. Such adjuvants include, but are not limited to, various oil formulations such as Freund's complete adjuvant, the dipeptide known as MDP, saponins, as disclosed for example in U.S. Pat. No. 5,047,540, aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes as disclosed for example in U.S. Pat. No. 4,235,877.

In a particular embodiment, the vaccine further comprises an additional active immunizing agent to produce a vaccine capable of inducing immunity against a number of different pathogens. The additional active immunizing agent may be an attenuated or inactivated form of a pathogen. Such a pathogen may be for example, rabies virus, *Borrelia burgdorferi*, canine distemper virus, canine parvovirus, canine adenovirus, canine corona virus, *Giardia* spp., *Leptospira interrogans, Babesia canis, Hepatozoon canis, Dipylidium caninum, Isospora* spp, or a combination thereof.

It is to be understood that while the attenuated *E. canis* strain and the vaccine comprising the attenuated *E. canis* strain not require an adjuvant for inducing an immune response, any additional immunizing agent, such as the aforementioned may require such a non-specific immune stimulator.

Also encompassed by the invention is a method of preventing ehrlichiosis in a susceptible mammalian host, wherein the method comprises administering an effective immunizing amount of a vaccine comprising an attenuated strain of *E. canis*, such as PCM B/00023, or an attenuated strain having substantially the same immunizing properties as PCM B/00023. In a particular embodiment, the administering is via a route selected from the group consisting of parenteral, oral, and intranasal administration. In a particular embodiment, the vaccine further comprises at least one pharmaceutically acceptable carrier. Other particular embodiments are as hereinbefore disclosed.

Methods of preparing and using vaccines, and general details of vaccine formulations including antigen amounts, route of administration and adjuvants are disclosed for example, in Remington's Pharmaceutical Sciences (1990) $18^{th}$ ed. Mack Publishing Co., Easton, Pa., Osol (ed.); New Trends and Developments in Vaccines (1978) Voller et al (eds.), University Park Press, Baltimore, Md.; Kensil, (1996) Therapeutic Drug Carrier Systems 13:1-55; Livingston et al. (1994) Vaccine 12:1275, and Powell et al. (1994) AIDS RES, Human Retroviruses 10:5105.

The foregoing description of the specific embodiments will so fully reveal the general nature of the invention that others can, by applying current knowledge, readily modify and/or adapt for various applications such specific embodiments without undue experimentation and without departing from the brand concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The following examples are presented in order to more fully illustrate certain embodiments of the invention. They should in no way, however, be construed as limiting the broad scope of the invention. One skilled in the art can readily devise many variations and modifications of the principles.

EXAMPLES

Example 1

Serial and Alternate Passage of *Ehrlichia canis* in Two Different Types of Tissue Cell Culture A viable culture of *Ehrlichia canis* Israeli strain 611 was propagated by serial passage in DH82 cells for a period of about 2 years. After this period, propagation of the strain was continued by serial passage in J774.A1 cells, as described in (9). Propagation in J774.A1 was carried out for a period of about 3 years. Next, the ehrlichiae were alternately propagated in DH82 and in J774.A1, with serial passage carried out in each cell line for a period of about 2 months, for a total of about 1 year. Finally, the ehrlichiae were propagated by serial passage in DH82 cells for an additional period of about 2 years, with each passage carried out every 7-10 days. The viability of the resultant strain was confirmed by culture.

Example 2

An Attenuated *E. canis* Strain Confers Protection Against Clinical Manifestation of Ehrlichiosis in Dogs While studying the minimal tick attachment time needed for the transmission of *Ehrlichia canis*, two dogs were experimentally infected with the strain of *E. canis* that had undergone multiple passages in two different cell cultures (DH82 and J774.A1 cells), as described in Example 1. After primary inoculation, the dogs exhibited a mild disease, indicated by thrombocytopenia with no apparent clinical signs. Intravenous challenge with a wild virulent strain of *E. canis* resulted in a mild clinical illness with no fever, compared to a severe disease in control dogs. The results of this study suggest for the first time that the multiple passages of *E. canis* in two different types of cell culture may lead to alteration and/or attenuation of ehrlichiae.

Materials and Methods
Experimental Ticks

Laboratory reared *R. sanguineus* ticks, free from infection with vertebrate pathogens were used in this study. The preimaginal stages were fed on gerbils (*Meriones tristrami*) and the adult ticks on rabbits as previously described (7). The non-feeding stages were maintained in an incubator at 27° C. and 80% relative humidity.

Experimental Infection of Dogs with *E. canis*

Two healthy 4-year-old beagle dogs (Nos. 10 and 11) vaccinated for distemper virus, parvovirus, parainfluenza, adenovirus-2, *Leptospira* and rabies were used in this study. The dogs were acclimatized to their new environment for 4 weeks before inoculation. The dogs were seronegative for *E. canis* antibodies as determined by indirect immunofluorescence antibody (IFA) assay, and no ehrlichial DNA was detected in a PCR assay using specific primers for *E. canis* at the time of infection. Their hematological and clinical chemistry parameters were within the normal reference range of the veterinary teaching hospital laboratory of the Hebrew University. During the course of the study they were held in a tick free animal facility.

The dogs (Nos. 10 and 11) were intravenously inoculated as previously described (8), with $10^6$ DH82 cells (macrophage cell line) heavily infected (>80% infection) with viable *E. canis* organisms, obtained following passage in two different cell lines, DH82 and J774.A1, according to the procedure described in Example 1.

Daily physical examinations including rectal temperature measurements were performed for both dogs during the acclimatization and post-infection (PI) period. Blood was drawn from the jugular vein before inoculation and thereafter at least three times weekly. Serum was separated after centrifugation within 1 hour of blood collection and stored at −70° C. until analyzed. Blood for hematology and PCR was collected in plastic tubes containing EDTA. Hematological analyses were preformed within 2 hours of blood collection using a semi-automatic impedance cell counter (Abacus, Diatron, Austria). The dogs were not treated against CME during the course of the study.

Serology for *E. canis* IgM and IgG antibodies was performed during the course of the study using the IFA test, as previously described (10). In addition, species specific nested PCR for detection of *E. canis* DNA based on the p30 gene was performed as previously described (11), before and after inoculation.

The study protocol was approved by and met all criteria set by the Hebrew University Animal Care and Use Committee.

Tick Infection Trials by Feeding on Infected Dogs

Laboratory-reared *R. sanguineus* larvae were fed on gerbils. After molting, the resulting nymphs were placed in ear bags on the experimentally *E. canis*-infected dogs as previously described (7, 12).

Two hundred and ten nymphs were placed in each ear bag (one bag for each dog) on day 23 PI when the dogs were rickettsemic as determined by PCR. The ear bags were checked daily for a period of 10 days until detached. Ticks that were not attached to the ears during the first 72 hours were discarded (a total of 30 nymphs). Both dogs were found to be rickettsemic on the day of detachment as determined by PCR. The p30-based nested PCR was performed on DNA extracted from the ticks after molting in order to detect tick infection with *E. canis*. DNA extracted from naïve ticks was used as a negative control, and *E. canis*-DNA extracted from *E. canis*-infected DH82 cells served as a positive control for the PCR assay.

Challenge Infection of Dogs Nos. 10 and 11 with a Wild Strain of *E. canis*

119 days post primary infection with *E. canis*-infected DH82 cells, the two dogs (Nos. 10 and 11) were challenged intravenously with 5 ml of heparinized blood, drawn from a clinically ill, PCR-confirmed naturally *E. canis*-infected dog. Simultaneously, five additional dogs were inoculated in the same manner with the identical infection source in a different experiment and were used as controls for the current study (6). The p30-based nested-PCR for *E. canis* was performed on blood drawn from the two dogs, before and after challenge inoculation as previously described (11).

Results
Infection of Dogs Nos. 10 and 11 with Cultured *E. canis*

Figure 2:
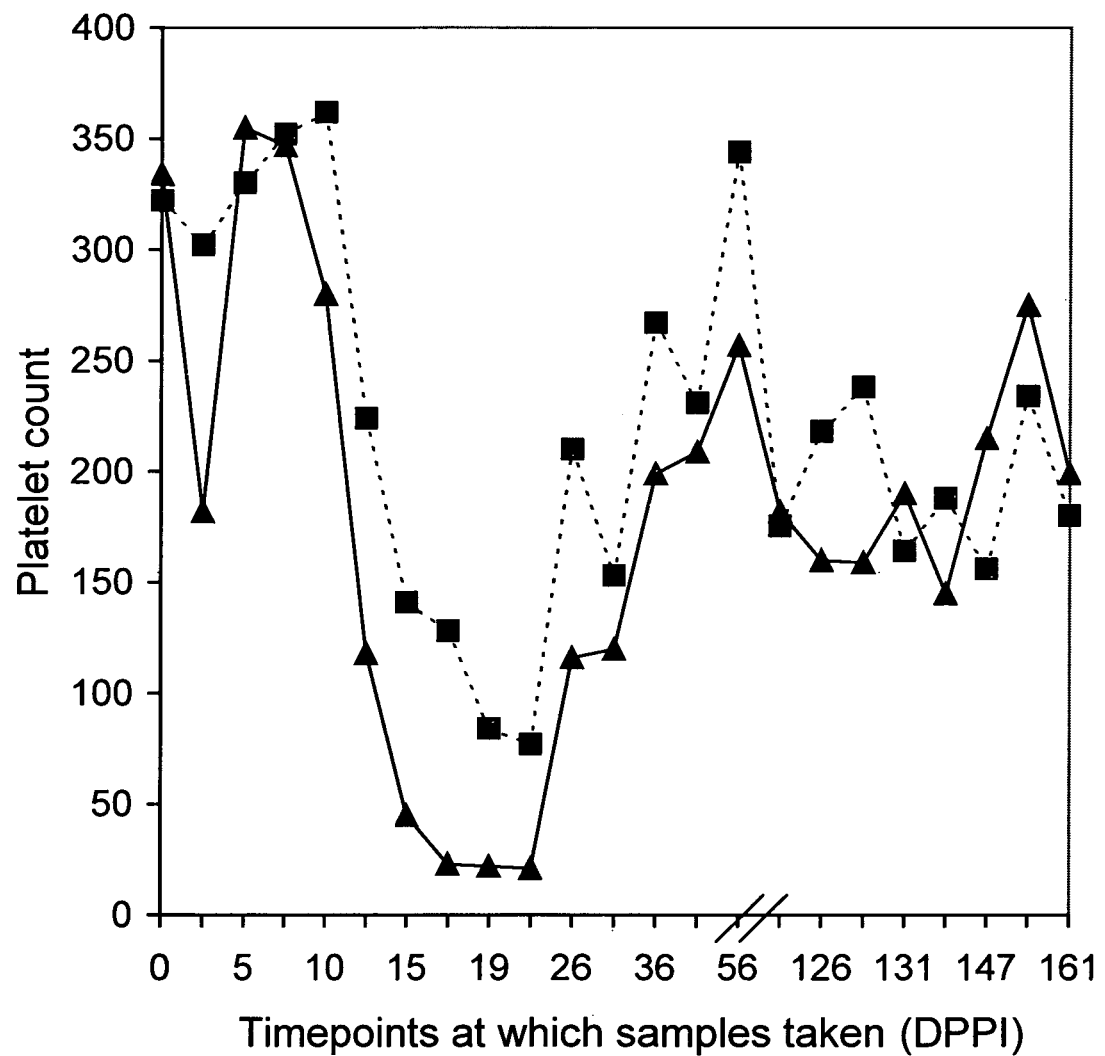
FIG. 2 illustrates mean platelet counts ($\times 10^3/\mu l$) of dogs No. 10 and No. 11 experimentally infected with *E. canis*, as described for FIG. 1.

Both dogs became infected with *E. canis* as confirmed by the seroconversion and positive PCR on day 12 PI. None of the dogs developed clinical signs, their rectal temperatures were within the normal reference range during the course of the study (FIG. 1), however both dogs developed pronounced thrombocytopenia that reached a nadir on day 23 PI of $21 \times 10^3/\mu l$ (dog No. 11) and $77 \times 10^3 \mu l$ (dog No. 10), (FIG. 2). No other hematological abnormalities were recorded.

Both dogs developed *E. canis* IgG antibodies, initially detected on day 12 post primary infection (Table 1). Low IgM titers were detected only twice during the primary infections, on days 16 and 21 PI for dog 11, and on days 12 and 16 PI for dog 10. In contrast, IgG levels increased rapidly and were greater than 1:1280 for both dogs from day 16 PI onwards.

Tick Feeding Trials on Infected Dogs

Trials to infect ticks by feeding on infected dogs (Nos. 10 and 11) resulted in no detectable tick infection, as manifested by the negative PCR results.

Challenge Infection of Dogs Nos. 10 & 11 with a Wild Strain of *E. canis*

Dog No. 11 showed mild petechiation and splenomegaly on day 42 post challenge (day 161 post primary infection), however dog No. 10 showed no clinical illness post challenge infection. Both dogs did not have fever and their platelet counts remained mildly thrombocytopenic post challenge for a period of 42 days (FIGS. 1 and 2). Other hematological findings were within the normal reference range. Both dogs (Nos. 10 and 11) had high levels of *E. canis* IgG-antibodies on the day of challenge and during the course of the study (Table 1). Both dogs were PCR negative on the challenge day (prior to challenge) and PCR positive on days 7, 11, 28 and 42 post challenge.

TABLE 1

| IgM and IgG antibody responses of dogs Nos. 10 and 11. | | | | | | | | | |
|---|---|---|---|---|---|---|---|---|---|
| DPPI | 0-7 | 12 | 16 | 21 | 28 | 35 | 42 | 119* | 126-191 |
| Dog 10 IgM | — | 1:160 | 1:80 | — | — | — | — | — | — |
| Dog 10 IgG | — | 1:1280 | >1:1280 | >1:1280 | >1:1280 | >1:1280 | >1:1280 | >1:1280 | >1:1280 |
| Dog11 IgM | — | — | 1:80 | 1:640 | — | — | — | — | — |
| Dog 11 IgG | — | 640 | 1:1280 | 1:1280 | 1:1280 | 1:1280 | 1:1280 | 1:1280 | >1:1280 |

DPPI—Day post primary infection.
*Day 119 post primary infection = day of challenge infection with the wild strain.

All five dogs in the concurrent control experiment developed clinical and hematological signs consistent with *E. canis* infection and canine ehrlichiosis, including fever, anorexia, depression, splenomegaly, and thrombocytopenia (6). *Ehrlichia canis*-DNA was detected in blood samples of all five dogs by days 7-10 PI, and they all seroconverted by day 12 PI. All five dogs developed a severe illness that endangered their lives and forced the inventors to initiate treatment with doxycycline on day 12 PI (6).

Discussion

The current trial to infect ticks by feeding on *E. canis*-rickettsemic dogs resulted in failure. The ticks were allowed to begin feeding on the 2 reservoir dogs during the acute stage of infection (day 23 PI) to increase the likelihood of tick infection, as previously suggested (3, 13, 14). Failure to transmit *E. canis* to ticks by feeding unengorged nymphs on dogs infected with cultured *E. canis* was previously described in a single report (13). However, in the latter report, the agent maintained its infectivity and pathogenicity for dogs as opposed to our canine experimental infection results. The difference between the results in the two studies may be related to the greater number of passages of the organism in tissue culture and to the use of a different non-canine culture cells (J774.A1) as additional transfer media in the present study. The findings of Mathew et al. (1996) and our results suggest that the *rickettsia* might have lost its infectivity for *R. sanguineus* during the repeated passages in culture cells (13). The organism might have undergone some changes which might have affected its affinity to the tick. Down-regulation of rickettsial binding proteins/receptors might explain the latter findings.

The possible changes in the organism may also be associated with the mild disease that was developed in both inoculated dogs. Both dogs (Nos. 10 and 11) developed thrombocytopenia with no apparent clinical signs of canine ehrlichiosis post inoculation with cultured *E. canis*. Previous inoculations of dogs with a similar isolate of *E. canis*, which however, had been cultured for only a few passages, with a similar inoculum size and a similar infection route, evoked severe clinical signs including pyrexia seen at day 10 PI, anorexia and generalized lymphadenomegaly, in each of 6 dogs participating in the study (8). It appears that the multiple passages over a number of years in DH82 and J774.A1 cells led to attenuation of the organism, resulting in a decreased pathogenicity hence produced a less severe disease.

The intravenous challenge of the two dogs (Nos. 10 and 11) with a wild strain of *E. canis* 119 days post primary infection, resulted in a mild illness with no fever (FIG. 2). The platelet counts of both dogs were however mildly thrombocytopenic post challenge (FIG. 2). The same inoculum source, quantity and infection method were used simultaneously in a parallel study in five other naïve dogs (of the same age) from the same colony that were never exposed to *E. canis* prior to the experimental infection and were used as controls for the current study. However, in contrast to the results of the current study, inoculation with the wild strain resulted in a severe illness in all five dogs, that endangered their lives and forced the inventors to start treatment on day 12 PI (6). While, a previous study showed that *E. canis* may persist in blood of infected dogs for years post infection (15), the blood of both dogs in the current study (Nos. 10 and 11) was found to be PCR-negative for *E. canis* on the day of challenge infection (four months post primary infection), suggesting the spontaneous elimination of the organisms from their blood. The absence of the ehrlichiae from the blood of the dogs at such an early stage, four months PI, appears to be the result of the ehrlichial attenuation. The latter finding, together with the mild thrombocytopenia, the absence of clinical signs in one dog and the mild clinical signs in the other dog post challenge infection with a virulent strain of *E. canis*, suggest that these dogs were immunized by the primary inoculation. Splenic aspirates were not drawn from the two challenged dogs (with the wild strain) on the day of challenge, therefore the possibility exists that ehrlichial organisms were present in the spleen while being absent from the blood (15). Our findings suggest that attenuated *E. canis* may be used in the development of an effective vaccine for CME.

The serological IgM response to *E. canis* in both dogs appeared sporadic and inconsistent, consistent with a previous report (18), and suggesting that measuring IgM is neither reliable nor useful in the diagnosis of *E. canis* infection. In contrast to the IgM response, the IgG concentrations increased rapidly and remained high during the course of the study (Table 1), emphasizing their diagnostic value in screening and defining exposure to *E. canis*.

In conclusion, the results of the experimental and challenge infections in this study suggest, for the first time, that *E. canis* that has undergone attenuation after multiple passages in two different cell cultures can serve as a potential vaccine candidate for CME.

REFERENCES

1. Ristic M, Huxsoll D L, Weisiger R M, Hildebrandt P K, Nyindo M B A. Serological diagnosis of tropical canine pancytopenia by indirect immunofluorescence. *Infect. Immun.* 1972; 6: 226-231.
2. Groves M G, Dennis G L, Amyx H L, Huxsoll. D L. Transmission of *Ehrlichia canis* to dogs by ticks (*Rhipicephalus sanguineus*). Am. J. Vet. Res. 1975; 36: 937-940.
3. Lewis G E, Ristic M, Smith R D, Lincoln T, Stephenson E H. The brown dog tick *Rhipicephalus sanguineus* and the dog as experimental host of *Ehrlichia canis*. Am. J. Vet. Res. 1977; 38:1953-1955.

4. Harrus S, Waner T, Bark H. nine monocytic ehrlichiosis—an update. *Comp. Cont. Educ. Pract. Vet.* 1997; 19: 431-444.
5. Branger S, Rolain J M, Raoult D. Evaluation of antibiotic susceptibilities of *Ehrlichia canis, Ehrlichia chaffeensis*, and *Anaplasma phagocytophilum* by real-time PCR. *Antimicrob. Agents Chemother.* 2004; 48: 4822-4828.
6. Harrus S, Kenny M, Miara L, Aizenberg I, Waner T, Shaw S. Comparison of Simultaneous Splenic Sample PCR for Diagnosis and treatment of Experimental *Ehrlichia canis* infection. *Antimicrob. Agents Chemother.* 2004; 48:4488-4490.
7. Hadani A, Cvilich R, Rechav Y, Dinur Y. Some methods for the breeding of ticks in the laboratory. *Isr. J. Vet. Med.* 1969; 26: 87-100.
8. Waner T, Leykin I, Shinisky M, Sharbani E, Buch H, Keysary A, Bark H, Harrus S. Detection of platelet-bound antibodies in beagle dogs after artificial infection with *Ehrlichia canis. Vet. Immunol. Immunopathol.* 2000; 7:145-150.
9. Keysary A, Waner T, Strenger T, Harrus S. Cultivation of *Ehrlichia canis* in a continuous BALB/C mouse macrophage cell culture line. *J. Vet. Diagn. Invest.* 2001; 13:521-523.
10. Keysary A, Waner T, Rosner M, Dawson J E, Zass R, Warner C K, Biggie K L, Harrus S. Isolation, in vitro propagation and genetic characterization of *Ehrlichia canis* from dogs in Israel. Vet. Parasit. 1995; 62:331-340.
11. Stich R W, Rikihisa Y, Ewing S A, Needham G E, Grover D L, Jittapalapong S. Detection of *Ehrlichia canis* in canine carrier blood and in individual experimentally infected ticks with a p30-based PCR assay. *J. Clin. Microbiol.* 2002; 40:540-546
12. Samish M, Pipano E. Transmission of *Theileria annulata* by *Hyalomma excavatum. Parasitology.* 1982; 86:269-274.
13. Mathew J S, Ewing S A, Barker R W, Fox J C, Dawson J E, Warner C K, Murphy G L, Kocan K M. Attempted transmission of *Ehrlichia canis* by *Rhipicephalus sanguineus* after passage in cell culture. *Am. J. Vet. Res.* 1996; 57:1954-1958.
14. Bremer W G, Schaefer J J, Wagner E R, Ewing S A, Rikihisa Y, Needham G R, Jittapalapong S, Moore D L, Stich R W. Transstadial and intrastadial experimental transmission of *Ehrlichia canis* by male *Rhipicephalus sanguineu. Vet. Parasitol.* 2005; 131:95-105.
15. Harrus S, Waner T, Aizenberg I, Foley J, Poland A M, Bark H. Amplification of Ehrlichial DNA from dogs 34 month after infection with *Ehrlicihia canis. J. Clin. Microbiol.* 1998; 36:79-82.
16. Bool P H. Studies on *Ehrlichia canis* (syn. *Rickettsia canis*). *Acta Tropica* 1959; 16, 97-107.
17. Mahan S, Kelly P J, Mahan S M. A preliminary study to evaluate the immune responses induced by immunization of dogs with inactivated *Ehrlichia canis* organisms. *Onderstepoort J. Vet. Res.* 2005; 72:119-128.
18. McBride J W, Corstvet R E, Gaunt S D, Boudreaux C, Guedry T, Walker D H. Kinetics of antibody response to *Ehrlichia canis* immunoreactive proteins. *Infect. Immun.* 2003; 71:2516-2524.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:
1. An attenuated strain of *E. canis* having accession number PCM B/00023.
2. A vaccine comprising (i) an effective immunizing amount of the attenuated strain PCM B/00023 of claim 1, and (ii) a pharmaceutically acceptable carrier.
3. The vaccine of claim 2, substantially free of an adjuvant, or further comprising an adjuvant.
4. The vaccine of claim 2, formulated for parenteral, oral, or intranasal administration.
5. The vaccine of claim 2, further comprising an additional active immunizing agent, wherein the additional active immunizing agent is an attenuated or inactivated form of a pathogen selected from the group consisting of: rabies virus; *Borrelia burgdorferi*; canine distemper virus; canine parvovirus; canine adenovirus; canine corona virus; Giardia; *Leptospira interrogans*, and combinations thereof.
6. A method of treating ehrlichiosis in a susceptible mammalian host, the method comprising administering an effective immunizing amount of the vaccine of claim 2.

7. The method of claim 6, wherein the susceptible mammalian host is selected from the group consisting of: dog; wolf; fox; jackal; deer and human; or wherein the ehrlichiosis is caused by an organism selected from the group consisting of: *E. canis; E. chaffeensis; E. ewingii; E. muris; E. ruminantium; Anaplasma phagocytophilum; A. platys*, and *Neorickettsia risticii.*

8. An *E. canis* vaccine, wherein the vaccine comprises (i) an effective immunizing amount of an attenuated strain of *E. canis* having accession number PCM B/00023, and (ii) a pharmaceutically acceptable carrier, wherein the attenuated strain of *E. canis* is obtained from the *E. canis* strain: Israel 611.

9. The vaccine of claim 8, formulated for parenteral, oral, or intranasal administration.

10. The vaccine of claim 8, substantially free of an adjuvant, or further comprising an adjuvant.

11. The vaccine of claim 8, further comprising an additional active immunizing agent, wherein the additional active immunizing agent is an attenuated or inactivated form of a pathogen selected from the group consisting of: rabies virus; *Borrelia burgdorferi*; canine distemper virus; canine parvovirus; canine adenovirus; canine corona virus; Giardia; *Leptospira interrogans*, and combinations thereof.

12. A method of treating ehrlichiosis in a susceptible mammalian host, the method comprising administering an effective immunizing amount of the *E. canis* vaccine of claim 8.

13. The method of claim 12, wherein the attenuated strain of *E. canis* is obtained from a strain of *E. canis* selected from the group consisting of: Israel 611; Ebony; Broadfoot; Florida; Kogashima 1; Louisiana; Oklahoma; Venezuela; Sao Paulo; Jake; Demon; D J, and Fuzzy; or wherein the attenuated strain of *E. canis* confers resistance to one or more pathogenic strains of *E. canis.*

14. The method of claim 12, wherein the administering is via a route selected from the group consisting of parenteral, oral, and intranasal administration.

15. The method of claim 12, wherein the susceptible mammalian host is selected from the group consisting of: dog; wolf; fox; jackal; deer and human; or wherein the ehrlichiosis is caused by an organism selected from the group consisting of: *E. canis; E. chaffeensis; E. ewingii; E. muris; E. ruminantium; Anaplasma phagocytophilum; A. platys*, and *Neorickettsia risticii.*

* * * * *